(12) United States Patent
Holman et al.

(10) Patent No.: US 6,837,897 B2
(45) Date of Patent: Jan. 4, 2005

(54) LUMEN SUPPORT FOR WELDING

(75) Inventors: Thomas J. Holman, Minneapolis, MN (US); Kristi Flury, Maple Grove, MN (US); Scott A. Olson, Zimmerman, MN (US); Jan Seppala, Maple Grove, MN (US); Richard Dunn, Brooklyn Park, MN (US); Gina L. Sandvick, Eden Prairie, MN (US); Fernando DiCaprio, St. Paul, MN (US); Justin E. Plessel, Fridley, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 201 days.

(21) Appl. No.: 09/939,276

(22) Filed: Aug. 24, 2001

(65) Prior Publication Data

US 2002/0068966 A1 Jun. 6, 2002

Related U.S. Application Data (63) Continuation-in-part of application No. 09/684,255, filed on Oct. 6, 2000.

(51) Int. Cl.⁷ ............................ A61M 29/00; A61F 2/06
(52) U.S. Cl. ...................................... 606/194; 623/1.11
(58) Field of Search ........................ 606/194; 623/1.11, 623/1.12

(56) References Cited

U.S. PATENT DOCUMENTS

| | | | | |
|---|---|---|---|---|
| 4,603,089 A | | 7/1986 | Bampton | .................... 428/593 |
| 4,950,227 A | | 8/1990 | Savin et al. | .................... 604/8 |
| 5,108,416 A | | 4/1992 | Ryan et al. | .................. 606/194 |
| 5,324,269 A | * | 6/1994 | Miraki | ........................ 604/160 |
| 5,403,341 A | | 4/1995 | Solar | .......................... 606/198 |
| 5,443,498 A | * | 8/1995 | Fontaine | ........................ 623/1 |
| 5,460,608 A | * | 10/1995 | Lodin et al. | .................. 604/96 |
| 5,779,729 A | * | 7/1998 | Severini | .................... 623/1.15 |
| 5,827,265 A | | 10/1998 | Glinsky et al. | ................. 606/8 |
| 6,254,609 B1 | * | 7/2001 | Vrba et al. | .................. 606/108 |
| 6,443,980 B1 | * | 9/2002 | Wang et al. | ................ 623/1.11 |

FOREIGN PATENT DOCUMENTS

| | | |
|---|---|---|
| EP | 0 262 699 | 7/1987 |
| EP | 0 897 730 A2 | 8/1998 |
| WO | 00/41525 | 7/2000 |

OTHER PUBLICATIONS

U.S. patent application Ser. No. 09/684,255, filed Oct. 6, 2000, pending.

* cited by examiner

*Primary Examiner*—David O. Reip
*Assistant Examiner*—D. Jacob Davis
(74) *Attorney, Agent, or Firm*—Vidas, Arrett & Steinkraus, P.A.

(57) ABSTRACT

A medical device comprising a support member adjacent to a first member and a second member, the first and second members may be laser welded to one another by directing radiation absorbable by the first and second members at the first and second members. The support member is provided adjacent to the first member and is constructed and arranged to substantially reflect or substantially transmit radiation at one or more frequencies absorbable by at least one of the first member and the second member.

23 Claims, 6 Drawing Sheets

LUMEN SUPPORT FOR WELDING

CROSS-REFERENCE TO RELATED APPLICATIONS

This Application is a continuation-in-part application, claiming priority from U.S. application Ser. No. 09/684,255 filed Oct. 6, 2000, the entire contents of which is incorporated herein by reference.

BACKGROUND OF THE INVENTION

The use of retaining sleeves to retain a stent on a catheter has been disclosed in a number of patents including U.S. Pat. No. 4,950,227 to Savin et al., U.S. Pat. No. 5,403,341 to Solar and U.S. Pat. No. 5,108,416 to Ryan et al. One or more retaining sleeves typically retain the stent on the catheter when the stent is in an unexpended state. Upon expansion of the stent, the retaining sleeves release the stent.

Retaining sleeves may be attached to a catheter tube using a variety of methods. One method involves using an adhesive to bond the retaining sleeve to the catheter tube. Another method involves welding the retaining sleeve to the catheter tube. Welding may be accomplished by heating the retaining sleeve or by applying laser radiation to the retaining sleeve at a wavelength absorbed by the retaining sleeve. $CO_2$ lasers have proven to be particularly useful in this regard. Heating may also be accomplished through application of other forms of laser energy, radio frequency, application of heating blocks, or other suitable heat sources.

In laser welding a retaining sleeve, there is a potential to damage the catheter tube to which the sleeve is being welded in general and the inflation lumen in particular.

There remains a need for novel techniques for affixing retaining sleeves to catheter tubes.

All US patents and applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

BRIEF SUMMARY OF THE INVENTION

The present invention includes many different embodiments. Some of the embodiments are directed to balloon catheters in general and more particularly to balloon catheters used in angioplasty and medical device delivery procedures.

In one embodiment, the invention is directed to a tube for use as a medical catheter. The tube includes a welding region and a first member is welded to the tube at the welding region. The first member may be welded to the welding region by application of a laser frequency which is absorbed by the tube and by the first member. A support member is provided in the welding region of the tube. The support member does not substantially absorb radiation at the laser frequency. As a result laser radiation is directed at the first member and welding region of the tube to weld the first member to the tube.

In another embodiment, the instant invention is directed to a medical device delivery system comprising a catheter assembly having a first retaining sleeve receiving region and a medical device receiving region. An expandable medical device is disposed about the medical device receiving region of the catheter assembly. A first retaining sleeve is disposed about the first end of the expandable medical device and the catheter assembly. The medical device delivery system further comprises a first support member disposed coaxially about the first sleeve receiving region of the catheter assembly. Desirably, the first support member substantially reflects or substantially transmits radiation at one or more frequencies absorbable by the first retaining sleeve. The sleeve may be provided in the form of a sleeve, coil, or other suitable form.

In yet another embodiment, the invention is directed to a method of affixing a retaining sleeve to a catheter. A catheter comprising an outer shaft assembly with a retaining sleeve receiving region and an inner tube extending within the outer shaft assembly is provided. An inflation lumen extends within the outer shaft assembly. A support member is disposed about the inflation lumen at the retaining sleeve receiving region of the outer shaft assembly. An expandable medical device is disposed about the distal end of the inner tube. A retaining sleeve is disposed about the proximal end of the expandable medical device and the outer shaft assembly in the retaining sleeve receiving region. Sufficient radiation at a first wavelength absorbable by the retaining sleeve and outer shaft is directed at the retaining sleeve and outer shaft assembly to affix the retaining sleeve to the outer shaft assembly.

In accordance with the invention the support member may be embodied in a variety of forms and may be constructed from a wide range of materials. In one embodiment, the support member may be a solid tube of material desirably with a high hoop strength. An example of such a material is hypodermic tubing with a high hoop strength. The solid tube support member may be metallic, plastic or a combination thereof.

In yet another embodiment of the invention, the support member may have a braided configuration.

In yet another embodiment of the invention, the support member may be removable from the catheter assembly.

DETAILED DESCRIPTION OF THE INVENTION

While this invention may be embodied in many different forms, there are described in detail herein specific exemplary embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component.

The present invention is directed to novel medical catheters for use in balloon angioplasty and/or delivery of implantable medical prosthesis, and novel methods for making such medical catheters.

Figure 1:
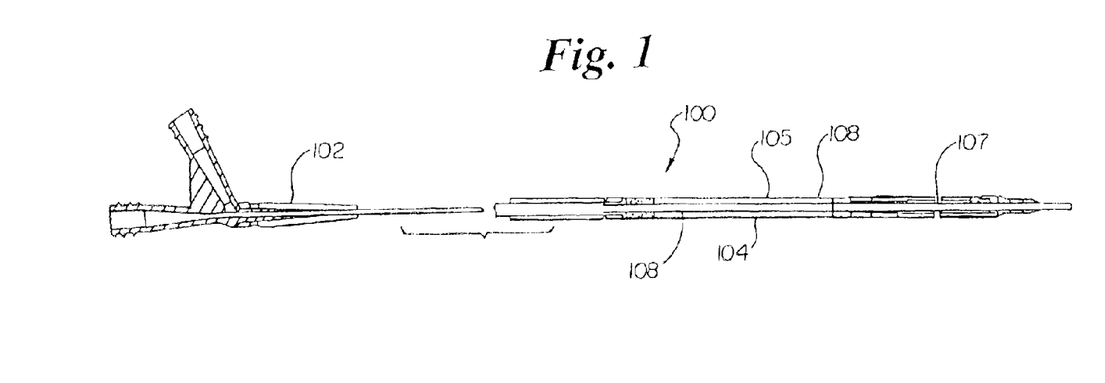
FIG. 1 is a longitudinal cross-sectional view of a medical device delivery system with portions enlarged.
Figure 2:
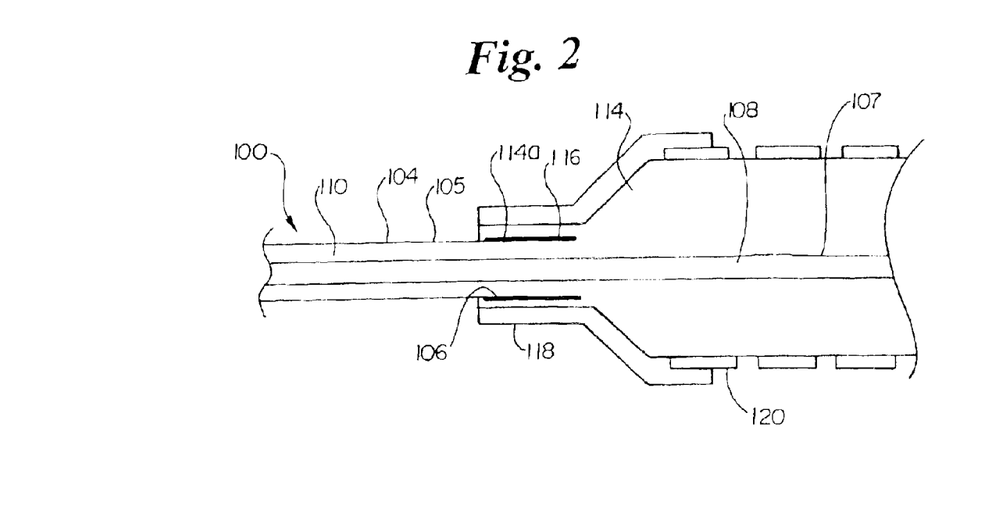
FIG. 2 is a longitudinal cross-sectional view of a portion of the distal end of a medical device delivery system with parts cut away.

In one embodiment, as shown in FIGS. 1 and 2, a medical device delivery system, shown generally at 100, comprises a catheter assembly 101. Catheter assembly 101 comprises a manifold 102 at the proximal end, an outer shaft assembly 104 and an inner tube 108. Outer shaft assembly 104 comprises an outer tube 105 having a retaining sleeve receiving region 106. Inner tube 108 extends within outer tube 105 and has a medical device receiving region 107. An inflation lumen 110 defined by the space between outer tube 105 and inner tube 108 extends within outer tube 105. The inflation lumen may also be provided as a separate tube extending within the outer tube or in any other suitable form. Outer shaft assembly 104 further comprises a medical balloon 114. The proximal end of the balloon is affixed at waist 114a to outer tube 105 via any suitable means including the use of adhesives and laser welding. The distal end of the medical balloon is affixed to inner tube 108 via any suitable means including the use of adhesives and laser welding. A stent 120 is disposed about medical balloon 114 and medical device receiving region 107 of inner tube 108. A support member 116 is disposed about inflation lumen 110 at retaining sleeve receiving region 106 of outer tube 105. Retaining sleeve 118 is laser welded to waist 114a of balloon 114 and extends over a portion of balloon 114 and stent 120.

In welding retaining sleeve 118 to waist 114a, radiation at a first wavelength absorbable by the retaining sleeve and the balloon is directed at the retaining sleeve and balloon. Sufficient radiation is directed thereto to at least partially melt the retaining sleeve and waist. The retaining sleeve and waist are then allowed to cool whereupon the waist and sleeve are mechanically engaged to one another.

Support member 116 prevents melting of the outer tube in the retaining sleeve region thereby preventing damage such as inward collapse of the inflation lumen that may otherwise occur in the absence of the support member.

Support member 116 desirably is made of a material that does not substantially absorb radiation at the wavelength absorbed by the balloon and the retaining sleeve. Within the context of the instant disclosure, a material which does not substantially absorb radiation at a given frequency does not absorb sufficient radiation at that frequency to heat the sleeve and cause melting of an adjacent portion of a tube.

Suitable materials for a support member include materials which are substantially reflective and/or substantially transmissive of radiation at the frequency used to laser weld the balloon and retaining sleeve. Such materials may be metals, polymers or others.

The material for the support member may absorb between about 5 to about 20 percent of the radiation directed at welding the balloon and retaining sleeve. Preferably, the support member absorbs between a bout 8 to about 12 percent of the radiation or less.

Polymer materials may prove to be particularly desirable in that in general they can provide the support strength of metal but with the added benefit of being flexible as well. Materials having a high melt temperature, such as for example, Poly-ether-etherkeytone or Polyether imide (Ultem™ from GE materials, for example), are even more desirable as they may provide support member 116 with sufficient melt resistance to avoid damage during the welding process as well as provide the support member 116 with a relatively high hoop strength.

Support member 116 may also be comprised substantially of metal, although the resulting support member 116 may tend to be rigid. Rather than providing the support member with such a rigid construction, the support member may alternatively be formed of a polymeric material with an extremely thin coating or film of metal, such as gold. If the metal coating is sufficiently thin, the support member 116 may have the requisite supportive strength characteristics of a more traditional metal tube, but due to the coating the support member may have improved flexibility when compared to other types of metal tubes. The thin metallic coating may be provided via a metalizing (sputtering) process, or any other suitable process.

Figure 13:
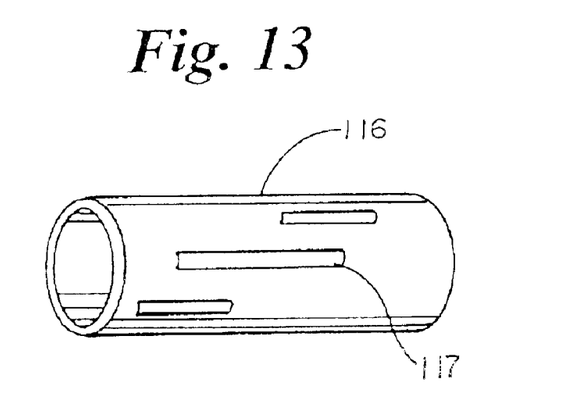
FIG. 13 is a side perspective view of an embodiment of a support member for use in the present invention.

As shown in FIG. 13, in yet another embodiment, support member 116 may be provided with improved flexibility by including one or more slots or cut-outs 117 along the length of the support member 116. Desirably, the slots are substantially oblong. Other shapes are also within the scope of the invention. Providing the support member 116 with one or more cut-outs or slots may provide an otherwise fairly rigid tube structure with the ability to flex and/or bend without substantially compromising the strength of the member.

Figure 3:
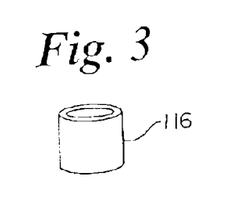
FIG. 3 is a schematic view of a support member in the form of a sleeve used in the accordance with the invention.
Figure 4:
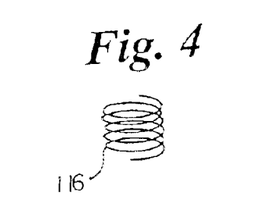
FIG. 4 is a schematic view of a support member in the form of a coil used in the accordance with the invention.
Figure 15:
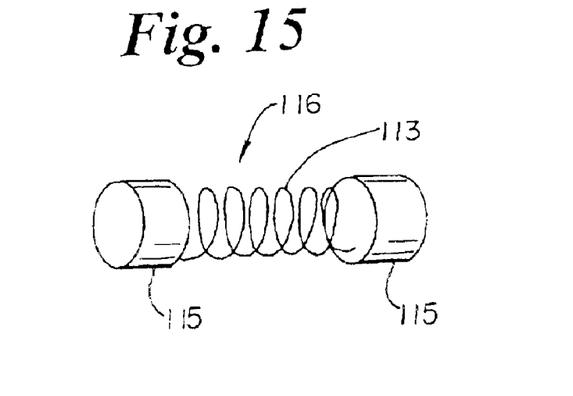
FIG. 15 is a schematic view of a support member in the form of a coil having solid ends.

Support member 116 may be in the form of a sleeve as shown in FIG. 3 or in the form of a coil as shown in FIG. 4. The coiled support member may be constructed from a variety of materials such as spring steel, stainless steel, Nitinol, and/or other metals and alloys thereof. Desirably, the coil is made of flat metal ribbon wound edge to edge. Alternatively, support member 116 may include a coiled middle portion 113 disposed between two solid ends 115, such as is shown in FIG. 15. Where the support is made of metal, the coil form allows for greater flexibility of the catheter in the region of the support member.

Figure 14:
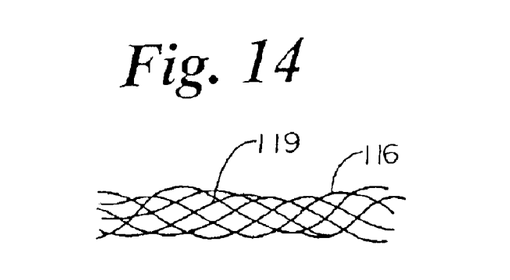
FIG. 14 is a side perspective view of an embodiment of a support member comprised of a plurality of braids for use in the present invention.

In yet another embodiment of the invention, the support member 116 may have a braided or woven configuration such as shown in FIG. 14. Like the coiled configuration described above, a braided support member may provide for improved flexibility of the catheter. A braided support member 116 may be constructed from a plurality of individual filaments or braids 119 of metal, plastic, or other suitable materials which may be woven together.

Figure 5:
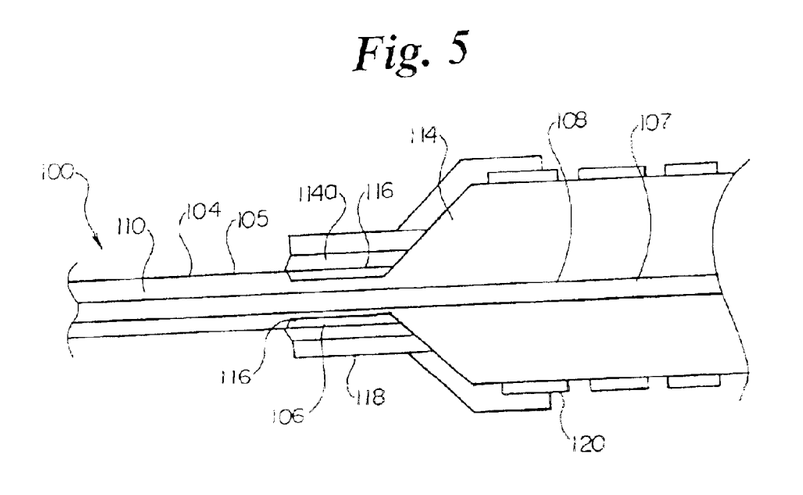
FIG. 5 is a longitudinal cross-sectional view of a portion of the distal end of a medical device delivery system with parts cut away.
Figure 6:
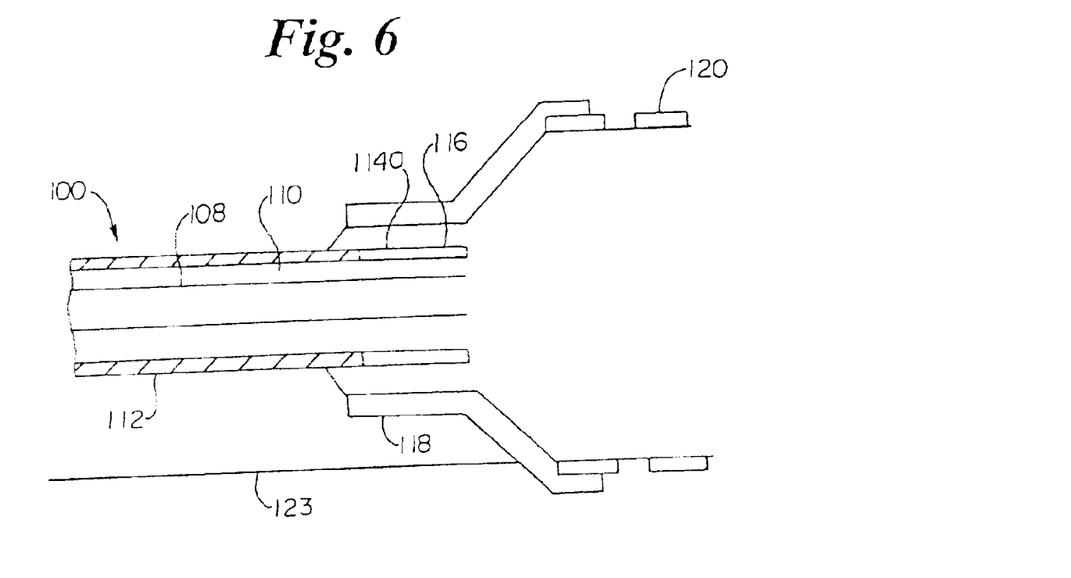
FIG. 6 is a side longitudinal cross-sectional of a portion of the distal end of a medical device delivery system with parts cut away.

Support member 116 may extend outward from outer tube 105 as shown in FIG. 2 or may be disposed interior to the outer tube as shown in FIG. 5. Support member 116 may also comprise a portion of outer tube 105 as shown in FIG. 6. This may be achieved by treating the support member portion of the outer tube differently from the remainder of the outer tube. For example, metal powder may be dispersed in the support member portion of the outer tube to render that portion reflective of radiation at the desired frequencies. Alternatively, the support member portion of the outer tube 105 may be co-extruded with the outer tube 105. For example a coil or braid of material different than that of the catheter could be extruded with the catheter matrix material to provide an integral lumen support without the need for the separate forms described above.

While the length of the support member is dependent on the application for which the support is used, it is believed that support members for use in bonding retaining sleeves are suitably about 3 mm to 7 mm in length and more suitably, about 5 mm in length. In determining the length of the support member, the length of the bond between the retaining sleeve and the balloon or catheter must be considered. Desirably, the support member will be approximately as long as the bond region if not longer As shown in FIG. 2, support member 116 will typically be positioned about inflation lumen 110 between outer tube 105 and waist 114a of balloon 114. In an alternative embodiment of the invention, support member 116 may be removed from about the retaining sleeve receiving region 106 subsequent to the welding procedure described above. Where support member 116 is removable, the support member may be drawn or pulled in a proximal direction off of outer tube 105.

Figure 7:
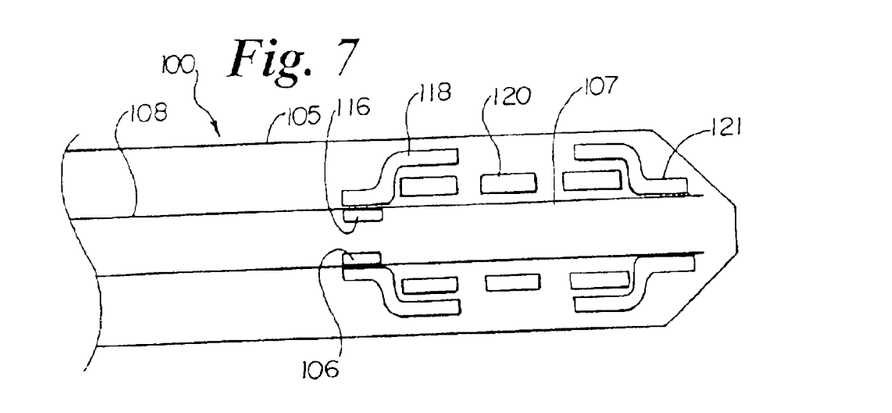
FIG. 7 is a longitudinal cross-sectional view of a portion of the distal end of a medical device delivery system with parts cut away.

The invention is also directed to medical device delivery systems which do not comprise medical balloons. As shown in FIG. 7, medical device delivery system 100 comprises inner tube 108 having a medical device receiving region 107 and a first retaining sleeve receiving region 106. Stent 120 is disposed about medical device receiving region 107. First retaining sleeve 118 is disposed about the proximal end of the stent and first retaining sleeve receiving region 106 of inner tube 108. Support member 116 is disposed interior to inner tube 108 at the first retaining sleeve receiving region 106 of the inner tube. Retractable outer sheath 105 is disposed about stent 120.

Any of the inventive medical device delivery systems described above may further comprise a second retaining sleeve. As shown in FIG. 7, second retaining sleeve 121 is disposed about the distal end of stent 120 and affixed to inner tube 108. In those embodiments comprising a medical balloon, the second retaining sleeve may be bonded to the balloon or to the inner tube.

First retaining sleeve 118 used in the inventive medical device delivery systems may be retractable from over the stent. As shown in FIG. 6, a retraction device comprising pull wire 123 may extend proximally from first retaining sleeve 118. Where present, the second retaining sleeve may also include a retraction device.

The retaining sleeves may be made from elastic and compliant balloon materials, including materials disclosed in U.S. Pat. No. 6,068,634. Suitable materials include those made of one or more thermoplastic elastomers i.e. block copolymers; copolymers and terpolymers of ethylene; homopolymers, copolymers and terpolymers of propylene; ethylene α-olefins; polyesters; polyamides; polyurethanes, such as TECOTHANE™ a biocompatable medical grade aromic polyurethane available from Thermedics, Inc.; polycarbonates, vinyl copolymers; ionomer materials and so forth. More specifically, materials such as nylon, SELAR™, polyether-polyester block copolymers (i.e. HYTREL™ from DuPont or ARNITEL™ from DSM, Netherlands), PEBAX™ (polyether block amide copolymers), SURLYN™, polyethylene terephthalate, polytetrafluoroethylene, polyvinyl chloride, polyetherurethanes, polyesterurethanes, polyurethane ureas, polyurethane siloxane block copolymers, silicone polycarbonate copolymers, ethylene vinyl acetate copolymers, acrylonitrile-butadiene-styrene copolymers; polyphenylene sulfides; copolyesters or other similar extrudable thermoplastic, polymeric materials, and/or composites thereof may be utilized.

Desirably, the retaining sleeves will be made of a material which is radiopaque, at least in part.

The medical balloon may be made of any suitable material including Pebax™. Other suitable materials are disclosed in U.S. Pat. Nos. 6,024,752, and 6,036,697.

Suitable materials for the outer tube are well known in the art and include high density polyethylene (HDPE) and SURLYN™ and those materials disclosed in U.S. Pat. Nos. 6,036,697 and 5,543,007.

The inner tube may be made of a flexible but substantially incompressible construction such as a polymer encapsulated braid or coil. The flexibility of the braid/coil allows the medical device delivery system to navigate through body lumens and the incompressibility of the braid/coil aids in maintaining the integrity of the system and aids in deployment accuracy when during release of the medical device.

The braid/coil may be comprised of stainless steel or Nitinol. Desirably the braid/coil comprises stainless steel encased in a polymer such as a polyimide, HDPE, Teflon or urethane, but desirably polyimide or Teflon. Other suitable materials which may be used are well known in the art.

The inventive medical device delivery systems disclosed herein may be configured as over-the-wire devices, as rapid exchange devices or as fixed wire devices. An example of an over-the-wire system is disclosed in U.S. Pat. No. 5,980,533. An example of a fixed-wire catheter is disclosed in U.S. Pat. No. 5,702,364 and an example of a rapid exchange U.S. catheter is disclosed in U.S. Pat. No. 5,534,007.

The inventive medical device delivery systems disclosed herein may also be provided with any of the features disclosed in U.S. Pat. Nos. 6,096,056, 6068,634, 6,036,697, 6,007,543, 5,968,069, 5,957,930, 5,944,726, 5,653,691 and U.S. Pat. No. 5,534,007.

The invention is also directed to methods of producing the inventive medical device delivery systems disclosed herein. In accordance with the inventive methods, a medical device delivery system may be produced by providing an outer tube with a support member as described above. The proximal waist portion of a balloon is disposed about the distal end of the outer tube and support member and a support mandrel inserted in the outer tube. Heat shrink tubing is disposed about the proximal waist portion of the balloon and shrunk to grip the waist. A laser beam is then directed at the waist to laser weld the waist to the outer tube. The heat shrink tubing may then be removed. In lieu of laser welding, the balloon may be adhesively bonded to the outer tube. Subsequent to laser welding or adhesive bonding, the mandrel may optionally be removed and a retaining sleeve laser welded to the balloon. An inner tube may be inserted in the outer tube and the distal waist of the balloon laser welded or otherwise bonded to the distal end of the inner tube. A stent or other expandable medical device may then be disposed about the inner tube. A retaining sleeve may then be disposed about the proximal end of the stent or other expandable medical device and laser welded to the inner tube in the region of the support member.

The mandrel may be of any suitable shape, including, for example: round or crescent. The mandrel supports the catheter during the welding process. The mandrel, as well as other removable support members disclosed herein, may be optionally coated with a release agent such as Teflon®, silicone and/or other agents. Where the mandrel or support member is constructed of plastic, a release agent may be necessary as the plastic support may become sticky when heated.

The support member may be provided between the outer tube and the balloon or interior to the outer tube. The support member may also consist of a portion of the outer tube as disclosed above.

The medical device delivery system may be subjected to additional processing steps prior to and/or subsequent to disposing the retaining sleeve about the stent and balloon. For example, bumpers and/or marker bands may be disposed about the inner tube or other portions of the medical device delivery system. A retractable sheath may be provided over the balloon and stent. A manifold may also be provided at the proximal end of the medical device delivery system. Other additional steps include providing to the inventive medical device delivery devices any of the features disclosed in U.S. Pat. Nos. 6,096,056, 6,007,543, 5,968,069, 5,957,930, 5,944,726 and U.S. Pat. No. 5,653,691.

The invention is also directed to a method of laser welding a first member to a tube in the production of a medical catheter. In accordance with the method, a tube for use in a medical catheter is provided. The tube has a welding region. A first member to be welded to the tube at the welding region is provided as is a laser operable at a laser frequency which is absorbed by the tube and by the first member. A support member which does not substantially absorb radiation at the laser frequency is provided in the welding region of the tube. Desirably, the support member will substantially reflect or transmit radiation at the laser frequency. The support member may be provided within the tube or may be disposed about the tube. Radiation is directed at the first member and welding region of the tube to weld the first member to the tube. Optionally, heat shrink tubing may be disposed about the tube or first member prior to laser welding and removed subsequent to laser welding. Additional support for the tube or first member may be provided by disposing a mandrel therein prior to welding.

In one embodiment of the inventive method, the tube comprises a balloon disposed at the distal end thereof and the first member is a retaining sleeve. Using the inventive method, the retaining sleeve may be welded to the balloon.

Figures 8, 9, 10:
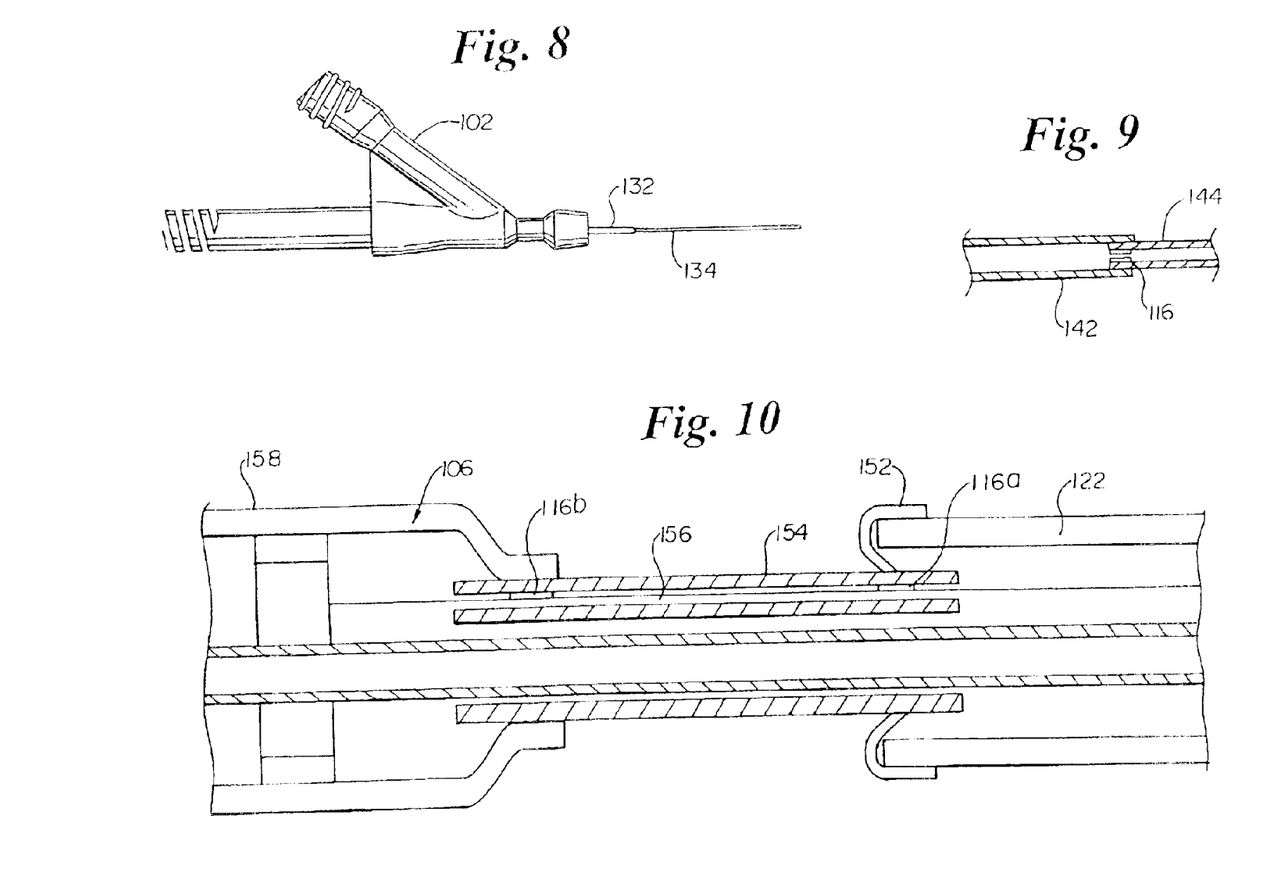
FIG. 8 is a side view of a manifold with a tube extending therefrom.
FIG. 9 is a longitudinal cross-section of a hypotube and midshaft tube.
FIG. 10 is a side cross-sectional view of a sliding seal.

In another embodiment of the inventive method, as shown in FIG. 8, the tube is hypotube 134 and the member is manifold 102 with tube 132 at the distal end. Hypotube 134 may be disposed about or within the distal end of tube 132. A support member 116 such as those disclosed above may be disposed within hypotube 134 or tube 132 depending on whether hypotube 134 is disposed in tube 132 or tube 132 is disposed in hypotube 134. Radiation at a frequency absorbable by the hypotube and manifold may be directed at the hypotube and manifold to weld the hypotube to the manifold.

In another embodiment of the inventive method, the tube is a hypotube and the member is a midshaft tube such as that disclosed in U.S. Pat. No. 5,957,930. As shown in FIG. 9, hypotube 142 may be disposed about a portion of midshaft tube 144 and a support member 116 such as those disclosed above disposed within the midshaft tube. The hypotube may also be disposed within the midshaft tube.

In yet another embodiment of the inventive method, as shown in FIG. 10, the member is a sliding seal 152 to be laser welded to a catheter tube 154 having a guidewire lumen 156 extending therethrough. In accordance with the inventive method, a support member 116a may be provided in tube 154 in the region where the sliding seal 152 is to be bonded to catheter tube 154. Radiation at a frequency absorbable by the sliding seal and tube may be directed at the sliding seal and tube to weld the sliding seal to the tube without damaging the guidewire lumen. A support member 116b may also be provided in the distal end of catheter tube 154 to support guidewire lumen 156 when catheter tube 154 and retractable sheath 158 are laser welded. Additional details about sliding seals may be found in U.S. Pat. No. 5,957,930.

Figure 11:
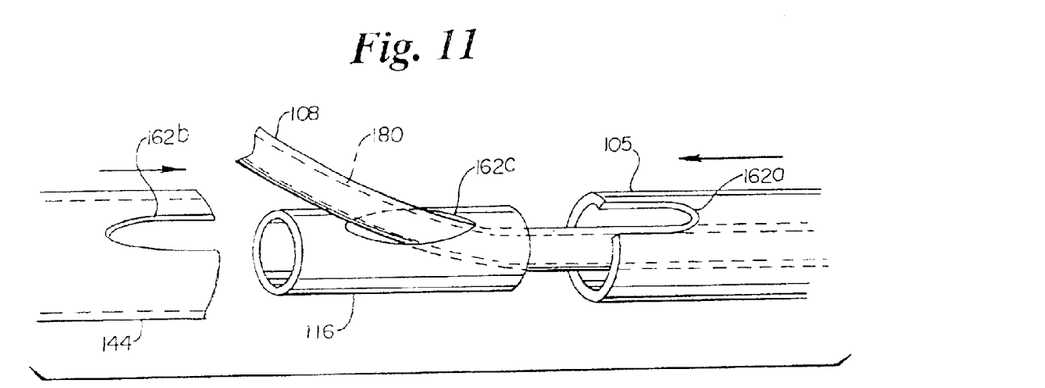
FIG. 11 is an expanded view showing the assembly of a portion of a rapid exchange medical delivery device at the guidewire port.
Figure 12:
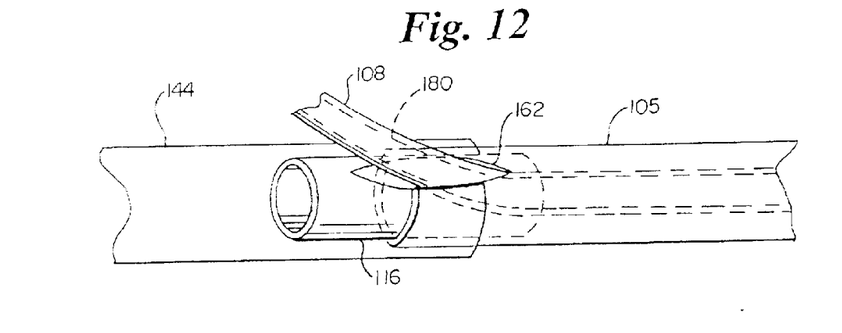
FIG. 12 is an assembled view of the portion of the rapid exchange medical delivery device of FIG. 11.

In yet another embodiment of the inventive method, as shown in FIGS. 11 and 12, the invention is directed to the assembly of a rapid exchange medical device delivery system. In accordance with the method, distal outer tube 105 having a notch 162a therein at the proximal end is provided as is midshaft tube 144. At least a portion of the distal outer tube 105 and/or at least a portion of the midshaft tube 144 may comprise a radiopaque material. Midshaft tube 144 has a notch 162b therein at the distal end. When midshaft tube 144 and distal outer tube 105 are assembled, notches 162a and 162b are aligned to form guidewire port 162. Tubular support member 116 having an opening 162c therein is also provided. Inner tube 108 enters tubular support member 116 through opening 162c and extends through the distal end of the tubular support member and into distal outer tube 105. Support for inner tube 108 is provided by support mandrel 180. As shown in FIG. 12, midshaft tube 144 and distal outer tube 105 are brought together with notches 162a and 162b aligned to form guidewire port 162 through which inner tube 108 with support mandrel 180 therein enters the assembly. Midshaft tube 144 and distal outer tube 105 overlap on support member 116. Radiation at a frequency absorbable by distal outer cube 105 and midshaft tube 144 is directed at the outer tube and the midshaft tube to weld the outer tube to the midshaft tube at guidewire port 162.

The invention is also directed to medical device delivery systems and catheters produced using the inventive methods.

The inventive medical device delivery systems disclosed herein may be used to deliver expandable medical devices including stents, grafts, stent-grafts, vena cava filters and other filters. Similarly, the inventive methods disclosed herein for constructing medical device delivery systems are applicable to the construction of delivery systems for expandable medical devices including stents, grafts, stent-grafts, vena cava filters and other filters.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

What is claimed is:

1. A medical device comprising:

a support member, a first tubular member and a second tubular member, the first tubular member being positioned immediately adjacent to at least a portion of the support member, the second tubular member being positioned immediately adjacent to at least a portion of the first tubular member, a portion of the first tubular member being welded to a portion of the second tubular member;

the support member constructed and arranged to substantially reflect radiation at one or more frequencies absorbable by at least one of the first tubular member and second tubular members;

wherein the support member is made of a polymeric material having a melt temperature in excess of the melt temperature of the second tubular member.

2. The medical device of claim 1 wherein the medical device is a catheter.

3. The medical device of claim 2 wherein the support member is a sleeve.

4. The medical device of claim 2 wherein the first tubular member comprises an inside surface and an outside surface, the support member being positioned immediately adjacent to the inside surface, the second tubular member being positioned immediately adjacent to the outside surface.

5. The medical device of claim 2 wherein the first tubular member comprises an inside surface and an outside surface, the support member being positioned immediately adjacent to the outside surface, the second tubular member being positioned immediately adjacent to the inside surface.

6. The medical device of claim 2 further comprising an outer tube, the support member being disposed about at least a portion of the outer tube.

7. The medical device of claim 6 wherein the first tubular member is a medical balloon.

8. The medical device of claim 7 wherein the second tubular member is a first retaining sleeve.

9. The medical device of claim 8 wherein the first retaining sleeve is welded to the medical balloon.

10. The medical device of claim 9 further comprising an inner tube, the outer tube disposed about at least a portion of the innner tube, the inner tube defining a lumen.

11. The medical device of claim 10 wherein the medical balloon has a proximal end and a distal end, the proximal end extending from the outer tube and the distal end extending from the inner tube.

12. The medical device of claim 10 wherein the catheler comprises an outer tube and an inner tube at least a portion of which is disposed within the outer tube, the support member disposed between the outer tube and the medical balloon.

13. The medical device of claim 9 further comprising a retraction device in mechanical communication with the first retaining sleeve, the retraction device extending to the proximal end of the medical device.

14. The medical device of claim 9 wherein at least a portion of the medical balloon defines a receiving region for an expandable medical device, the receiving region being adjacent to the frist retaining sleeve, the region constructed and arranged to receive an expandable medical device thereabout.

15. The medical device of claim 14 wherein the expandable medical device is a stent.

16. The medical device of claim 6 wherein the support member is integral with at least a portion of the outer tube of the catheter assembly.

17. The medical device of claim 2 wherein at least a portion of at least one of the first tubular member and the second tubular member is radiopaque.

18. The medical device of claim 1 wherein the support member is made of a flexible material.

19. The medical device of claim 1 wherein the support member is removable from the first tubular member.

20. The medical device of claim 1 wherein the support member is at least partially coated with a release agent.

21. The medical device of claim 1 wherein the support member is braided.

22. The medical device of claim 1 wherein the support member is comprised of a plurality of braids.

23. The medical device of claim 1 wherein the support member is constructed at least partially from hypotubing.

* * * * *